United States Patent
Bihari

(12) 
(10) Patent No.: US 6,288,074 B1
(45) Date of Patent: Sep. 11, 2001

(54) METHOD OF TREATING LYMPHOPROLIFERATIVE SYNDROME

(76) Inventor: Bernard Bihari, 29 W. 15th St., New York, NY (US) 10011

( * ) Notice: Subject to any disclaimer, the term of this patent is extended or adjusted under 35 U.S.C. 154(b) by 0 days.

(21) Appl. No.: 09/439,987

(22) Filed: Nov. 15, 1999

Related U.S. Application Data

(60) Provisional application No. 60/108,828, filed on Nov. 17, 1998.

(51) Int. Cl.$^7$ .................................................. A61K 31/44
(52) U.S. Cl. ........................ 514/282; 514/277; 514/279; 514/280; 514/281; 514/908
(58) Field of Search ................................... 514/277, 279, 514/280, 281, 282, 908

(56) References Cited

U.S. PATENT DOCUMENTS 5,631,263 * 5/1997 Portoghese et al. ................. 514/279

* cited by examiner

*Primary Examiner*—Dwayne C. Jones
*Assistant Examiner*—C. Delacroix-Muirheid
(74) *Attorney, Agent, or Firm*—William J. Daniel

(57) ABSTRACT

Lymphoproliferative syndrome, including such diseases as malignant lymphoma, chronic lymphocytic leukemia, Hodgkin's lymphoma, and non-Hodgkin's lymphoma, is treated in human patients by the administration by a pharmacologically effective mode or route of an essentially pure opiate receptor antagonist, typified by Naltrexone and Naloxone, exerting substantially higher blocking action for Mu opiate receptor sites than against Delta opiate receptor sites at a low dose concentration which produces therapeutic results corresponding to those obtained by the administration of Naltrexone at a low dosage level in the range of 1.0 mg. to 10 mg. and at which Delta receptor blocking activity is at most small and Mu receptor blocking activity is significant and most preferably substantially exclusive. Naltrexone is suitable for oral administration and is preferred.

6 Claims, No Drawings

US 6,288,074 B1

METHOD OF TREATING LYMPHOPROLIFERATIVE SYNDROME

CROSS-REFERENCE TO PROVISIONAL APPLICATION

This application is a complete application of my provisional application Ser. No. 60/108,828, filed Nov. 17, 1998.

SPECIFICATION

This invention relates to the treatment of lymphoproliferative syndrome and is concerned specifically with treatment of this syndrome, including by such diseases as malignant lymphoma, chronic lymphocytic leukemia, Hodgkin's lymphoma, and non-Hodgkin's lymphoma, by administration of an essentially pure opiate receptor antagonist such as Naltrexone and Naloxone at a low level dosage.

BACKGROUND

The use of an essentially pure opiate receptor antagonist in the treatment of several diseases has already been disclosed in patents in which I am named as an inventor. In U.S. Pat. No. 4,888,346, issued Dec. 19, 1989, the treatment was for the acquired immune deficiency syndrome (or AIDS) in any of its known states, including AIDS-related complex. In U.S. Pat. No. 5,013,739, issued May 7, 1991, the disease treated was chronic fatigue syndrome while in U.S. Pat. No. 5,346,900, issued Oct. 18, 1994, the disease was chronic herpes virus infections. In the latter patent, examples of treatment of multiple sclerosis was also disclosed.

For the treatment of all these diseases, the amount of the essentially pure opiate receptor antagonist was required to be at a quite low level corresponding in results to those obtained by the administration of Naltrexone at a dosage level of from 1.0 mg. to 10 mg., preferably at a dosage level of 1.0 mg. to about 5 mg., and most preferably up to about 3.0 mg. At dosage levels above about 10 mg., not only were the desired therapeutic results not obtained but the effect of the treatment appeared to be negative in acerbating the disease.

I have now discovered that administration of an essentially pure opiate receptor antagonist gives desirable and beneficial therapeutic results in the treatment of a group of closely related malignancies known as lymphoproliferative syndrome, which includes malignant lymphoma, chronic lymphocytic leukemia, Hodgkin's disease (or Hodgkin's lymphoma), and non-Hodgkin's lymphoma. As the generic name suggests, these diseases are characterized by the multiplication or proliferation of tissue of the lymphatic system, especially lymphocytes (cells) produced in the lymph nodes. Lymphocytes are important components of the human immune response system and upon exposure to a foreign antigen in the human body naturally proliferate or multiply to combat the antigen. In this group of malignancies, the proliferation goes out of control, resulting in an abnormal level of lymphocytes in the blood stream, enlargement of the lymph nodes due to accumulation of the lymphocytes there, and other symptomatic characteristics.

In the past, these diseases were generally treated by radiology and chemotherapy often employing a combination of antineoplastic agents. I have discovered that the lymphoproliferative syndrome can respond to an entirely different therapeutic approach involving the administration of essentially pure opiate receptor antagonists at the same relatively low quantitative level that was found useful for the treatment of the disorders disclosed in the above-specified patents despite the totally different nature of the earlier diseases which did not involve any malignant behavior.

It is not possible to provide any coherent rationale for the therapeutic effectiveness of an essentially pure opiate receptor antagonist against the diseases falling within the lympholiferative syndrome. Indeed, any therapeutic activity of these antagonists for the lymphoproliferative syndrome would appear from general principles of immune action to be highly unlikely if not entirely out of the question. It is generally believed that the immunocompetent action of lymphocytes arises out of some surface structural feature, usually called "receptor", that is capable in some way of "recognizing", perhaps by "capture", some structural feature of an invading foreign antigen. This "recognition" mechanism, whatever its nature, initiates the production of antibodies effective against the particular antigen. Even assuming that lymphocytes have receptors for opiates, it is quite puzzling that blocking of these receptors by an opiate antagonist would in some way interfere with whatever is the causative factor or factors in lymphatic cancers.

If an occurrence of the lymphoproliferative syndrome could be traced strongly to viral or bacterial action and if such action is assumed to involve receptor sites on lymphocytes, one could possibly theorize that an opiate receptor antagonist might be preferentially blocking such sites and preventing any connection with viral or bacterial particles. However, viral and bacterial sources are usually accepted as having a limited association with any disease of the lymphoproliferative syndrome and this theory thus could hardly apply to all of the diseases of this syndrome.

In any case, while such an association might explain how administration of an opiate receptor antagonist could reduce the likelihood of the original initiation of the malignancy, it would not explain how such administration could provide a therapeutic action after the malignancy has progressed to the point of treatment. It is true for lymphatic cancers as for all cancers that at the time diagnosis is possible, the cancer is necessarily at a well-developed, if not "advanced", stage of development. Receptor site preclusion cannot therefore explain an interference with a malignant proliferation of the lymphocytes. This is particularly true since the presence of the opiate receptor antagonist does not appear to block normal proliferation of the lymphocytes in the system and their differentiation into B- and T-type cells as is essential to a viable immune function.

McLaughlin et al have disclosed in U.S. Pat. No. 4,689,332; among others, that opiate receptor antagonists. exemplified by Naltrexone and Naloxone, when administered to a variety of living organisms, including tissue and cells, can exert either a growth accelerating or a growth inhibiting effect dependent upon the length of time the opiate receptor sites of the organism are "completely and continuously" blocked or occupied by the antagonist. Specifically, a growth accelerating or promoting action occurs with blockage for a period of at least 12 hours per day, as can be achieved with a dosage of at least about 10 mg. and preferably about 20 mg. per day, whereas a growth inhibiting action occurs with blockage for only a period of about 2 to 12 hours per day, as can be achieved with a dosage of less than 10 mg. down to about 0.1 mg. per day.

The growth accelerating embodiment is said to be effective "to proliferation, migration, and differentiation of certain specific cells or tissue, including organ tissues, neural tissue, bone marrow, red blood cells, lymphocytes, liver cells, etc." (See patent, col. 9, lines 15–25.) This disclosure, however, is silent as to whether these any of these same "cells or tissues" can be subject to the growth inhibiting embodiment, the focus of the inhibiting embodiment disclosure paralleling the above excerpt being on weight loss of the organism as a whole. (See col. 9, lines 32–45 and col. 10, lines 45–59.)

In addition, the growth inhibiting aspect is described as "related to the prevention, treatment and control of cancer" (see col. 10, line 60—col. 11, line 47), the essential disclosure in this connection being as follows; "The action of the compounds of the invention can be employed to terminate the rapid growth patterns of cancer and related abnormalities. It should be understood, that a regime of the present compounds cannot dissipate or reduce a tumor mass or other metastasized growth. These compounds can only terminate the growth of the abnormal cells and inhibit the continued growth thereof. However, by preventing tumor growth to continue [sic], i. e. reducing the tumor burden, the body's own defense mechanism, i. e. the immune system, has the opportunity to rid the body of the cancerous growth whether benign or malignant. This aspect of the invention is particularly significant in light of early diagnostic techniques which do reduce tumor size, or with procedures for tumor excision. Moreover, naloxone, naltrexone, or the other related compounds can be administered as a prophylaxis to human or animal subjects who may be exposed to potentially carcingenic [sic] agents."

The only cancer specifically identified for treatment in McLaughlin et al. patent is neuroblastona in mice, as illustrated by specific examples 2, 3, and 5, the only examples concerned with cancer. Neuroblastoma is a rather rare and special type of cancer, occurring in the sympathetic autonomous nervous system, i. e. mainly the nerves of the spinal column, and is essentially limited to young children up to about 10 years of age. Evidence has been reported that neuroblastoma is peculiarly susceptible to natural immunobiological resistance. According to "IMMUNOBIOLOGY POR THE CLINICIAN" by Barber, Copyright 1977, John Wiley & Sons, the lymphocytes of disease-free mothers of young neuroblastoma patients have the capacity to kill neuroblastoma cells extracted from their diseased children but had no effect on normal tissue cells or tumor cells of other than neuroblastoma and that lymphocytes of siblings of such patients also were able to kill neuroblastoma cells of the patients. (Cf p. 69). The same text states (at p. 102) that incidence of neuroblastoma nodules found by autopsy is "40–50 times greater" than the overall incidence of clinically diagnosed neuroblastoma. This obviously suggests that a competent immune system exerts a strong controlling action on neuroblastoma which is found in few other kinds of cancers.

While there is a tendency among the general public (and even the often equally uninformed media) to generalize between all "cancers", (a conception which unfortunately appears to be shared by McLaughlin et al) "cancer" is, in fact, a collection of many distinct malignancies, each with its unique characteristics, behavior, and treatment response (which is one reason for the tortuously slow progress in the treatment of "cancer"), and this individualistic nature is especially applicable in the case of neuroblastoma. One cannot, therefore, reasonably extrapolate from the response of neuroblastoma to a given prophylaxis to a supposition that an entirely different type of "cancer" will exhibit the same response and this conclusion is particularly valid in the case of lymphoproliferative malignancies.

As already noted above, lymphocytes are at least a core component, if not the keystone, of the body's immune system which is an important, if not the principal, mechanism by which the body attacks and controls cancers generally. It is the lymphocytes, or their derivatives, which recognize the foreign antigenic nature of cancer cells or of antibodies associated therewith and attack the cancer cells. The route set forth by McLaughlin et al. for controlling "cancer" by their treatment, as quoted above, does not make sense when it is the lymphocytes themselves that are malignant. How can proliferation of malignant lymphocytes be inhibited without at the same time inhibiting the natural proliferation of normal lymphocytes essential to effective functioning of the immune system? Further, if the object of the treatment is, as stated, to reduce the extent of the cancer to a degree within the capacity of the immune system (lymphocytes) to control, how does an active "normal" lymphocyte recognize a malignant lymphocyte?.

For at least these reasons, therefore, the discovery that essentially pure opiate receptor antagonists, such as naltrexone or naloxone, exert therapeutic action against the lymphoproliferative syndrome is believed to be unexpected if not remarkable.

The diseases usually identified within the lymphoproliferative syndrome have been previously identified and their symptoms and other characteristics can be found in abbreviated form in any medical encyclopedia, such as "Miller-Keane Encyclopedia & Dictionary of Medicine, Nursing, & Allied Health", 5th Edition, 1992, W. B. Saunders Co. or in more expanded form in any medical text, such as for example "Cecil Essentials of Medicine", by Andreoli etal, Copyright 1986 by W. B. Saunders Co. At present, the four diseases identified are considered to constitute the lymphoproliferative syndrome but if other diseases should be characterized by excessive proliferation of lymphocytes, they too would respond to the present therapy and should be deemed within the scope of the invention.

Similarly, while Naltrexone and Waloxone are presently the only essentially pure opiate receptor drugs known to have received government approval for administration to humans, if other drugs exist or should be developed exhibiting the same preferential or selective affinity for Mu over Delta opiate receptor sites, they too should be effective for purposes of the present method and are within the scope of the invention. For more details of this selective or preferential action, reference may be had to U.S. Pat. No. 5,013,739, the relevant portions of which, in particular col. 5, line 17—col. 6, line 25, are incorporated by reference.

Similarly, while the dosage levels have been briefly specified above, more complete information as to dosage level which is applicable to the present invention, is given in the same -739 U.S. patent, especially col. 6, line 59—col. 7, line 17, which is incorporated by reference. In as much as Naltrexone is available in a form suitable for oral administration and is recognized to be effective when so administered, it is preferred that the Naltrexone be utilized as the opiate antagonist and be administered orally, but where effective other administration routes are, in principle, not precluded and can be employed. Naloxone, on the other hand, has not generally proven to be effective when administered orally; it is available in a form suitable for injection and is better administered by injection, It is also preferred that administration take place in the evening hours, and particularly at bedtime, since the action of the antagonist appears to develop more strongly when the patient is sleeping and at rest.

EXAMPLES

Example 1

A 37 year old female patient had been diagnosed 3½ years earlier as having non-Hodgkins lymphoma and had been successfully treated into remission with chemotherapy by an oncologist in a different state. With this treatment, the symptoms experienced during the active phase of her disease, namely, tumor masses and associated weight loss, fevers, low energy, life-threatening systemic infections, and malaise, had all cleared and she enjoyed this remission for three years. Then, however, lymphoma reappeared in lymph glands in her neck, chest, and abdomen and her earlier symptoms of fevers, malaise, weight loss, reduced energy, and increased vulnerability to systemic infections recurred. Lymph node biopsy was positive for lymphoma and chemotherapy was reinstituted. She did not respond to chemotherapy and her disease was judged to be resistant to this therapy. Six months after this recurrence began, her weight loss had reached 20 pounds, she had enlarged lymph nodes in her axilla and groin, an enlarged spleen, an elevated white blood cells count with a number of atypical lymphocytes, and was naturally quite frightened at her condition.

She was started on Naltrexone at 3 mg. by mouth every night at bedtime. After 3 weeks, her fever began to subside and after 3 months, all of her symptoms had cleared without treatment other than the Naltrexone. After about 4 months of Naltrexone treatment, she was examined by her original oncologist and her related lab work repeated, which showed that her X-ray and blood abnormalities had cleared. She had regained her lost weight, was free of all other symptoms and was adjudged to be in full remission. The low dose Naltrexone treatment has been continued and after about one year, she remains in remission.

Example 2

A 38 year old man had been diagnosed by an oncologist as having Hodgkins disease based on symptoms of enlarged cancerous lymph nodes in the paravertebral areas of his chest and abdomen, an enlarged spleen, poor appetite, a 20-pound weight loss, malaise and fever. After receiving radiation and chemotherapy, these symptoms cleared, his weight loss was re-gained and he was declared to be in remission. After about four years, his symptoms recurred including the enlarged spleen, enlarged paravertebral nodes in his chest and abdomen as shown by X-ray, tiredness, loss of appetite, and weight loss. He was again treated with chemotherapy with no response and he was advised that his disease become resistant to chemotherapy.

Some 6 months subsequent to his reoccurrence and failed chemotherapy and following a new examination confirming the diagnosis of Hodgkins lymphoma, he was started on Naltrexone at 3 mg. by mouth every night at bedtime. After four months of taking Naltrexone at this dosage, his enlarged nodes and spleen shrank to normal size as revealed by X-ray film and Ct scans, his energy and appetite returned to normal levels and his weight loss regained, At this point, he was reevaluated by his oncologist and was told he was in remission. His Naltrexone therapy has continued for a total of about 3 years and he has remained free of all symptoms. During this time, X-rays at 6 month intervals and CT Scans at 12 month intervals have remained normal.

Example 3

A woman was examined and found to have three golf-ball size nodes in her groin which on biopsy were positive for non-Hodgkin's lymphoma. When she refused chemotherapy, she was started on Naltrexone at a dosage of 3 mg. by mouth qhs (i. e. every night at bedtime) and after 12 weeks her groin nodes disappeared. She continued on this Naltrexone treatment and remained free of nodes until her death four years later from arteriosclerotic heart disease (ASHD).

What is claimed is:

1. A method of treating a human patient suffering from lymphoproliferative syndrome, which comprises the step of administering by a pharmacologically effective mode to said patient a therapeutically effective dose of a therapeutic agent consisting essentially of an essentially pure opiate receptor antagonist having a selectively higher blocking action against Mu opiate receptors than against Delta receptors, the amount of said dose being selected to produce therapeutic results substantially corresponding to those produced by Naltrexone when administered in the range of about 1 mg to about 10 mg per day.

2. The method of claim 1 wherein said lymphoproliferative syndrome is selected from the group consisting of lymphoma, chronic lymphocytic leukemia, Hodgkin's lymphoma and non-Hodgkin's lymphoma.

3. The method of claim 1 wherein said antagonist is administered at bedtime of the patient.

4. A method of treating a human patient suffering from lymphoproliferative syndrome, which comprises the step of administering by a pharmacologically effective mode to said patient a therapeutic agent consisting essentially of an essentially pure opiate receptor antagonist having a selectively higher blocking action against Mu opiate receptors than against Delta receptors in an amount which is effective to exert a substantially higher opiate blocking action against Mu receptors than against Delta receptors.

5. The method of claim 4, wherein said opiate receptor antagonist is either naltrexone or naloxone.

6. The method of claim 4 wherein said lymphoproliferative syndrome is selected from the group consisting of lymphoma, chronic lymphocytic leukemia, Hodgkin's lymphoma and non-Hodgkin's lymphoma.

* * * * *